United States Patent

Rake et al.

[11] Patent Number: 5,911,716
[45] Date of Patent: Jun. 15, 1999

[54] PLATEN PUMP

[75] Inventors: Kenneth W. Rake, Laguna Niguel; Orvil L. Judge, Orange; Donald M. Earhart, Irvine, all of Calif.

[73] Assignee: I-Flow Corporation, Lake Forest, Calif.

[21] Appl. No.: 07/824,855

[22] Filed: Jan. 24, 1992

[51] Int. Cl.$^6$ .............. A61K 9/22; A61M 1/00; A61M 5/20; B65D 35/28

[52] U.S. Cl. .......... 604/890.1; 641/31; 641/135; 641/153; 641/891.1; 128/12; 222/95; 222/108

[58] Field of Search ............... 604/890.1, 31, 604/131–135, 140–143, 145, 146, 147, 150, 151, 153, 154, 155, 891.1; 128/DIG. 12, DIG. 13

[56] References Cited

U.S. PATENT DOCUMENTS

| | | |
|---|---|---|
| 3,029,983 | 4/1962 | Wagenhals . |
| 3,048,171 | 8/1962 | Grau ........................ 604/134 |
| 3,151,616 | 10/1964 | Selfon . |
| 3,384,080 | 5/1968 | Muller . |
| 3,451,393 | 6/1969 | Sarnoff . |
| 3,468,308 | 9/1969 | Bierman . |
| 3,469,578 | 9/1969 | Bierman . |
| 3,565,292 | 2/1971 | Jinotti . |
| 3,595,232 | 7/1971 | Leibinsohn . |
| 3,625,401 | 12/1971 | Terry . |
| 3,640,276 | 2/1972 | Dancy, Jr. . |
| 3,640,277 | 2/1972 | Adelberg . |
| 3,647,117 | 3/1972 | Hargest . |
| 3,670,926 | 6/1972 | Hill . |
| 3,731,681 | 5/1973 | Blackshear et al. . |
| 3,734,351 | 5/1973 | Gaudin . |
| 3,847,304 | 11/1974 | Cohen ........................ 222/105 |
| 3,895,631 | 7/1975 | Buckles et al. . |
| 3,895,741 | 7/1975 | Nugent . |
| 4,033,479 | 7/1977 | Fletcher et al. ............. 272/95 |
| 4,059,110 | 11/1977 | Wuthrich et al. . |
| 4,077,544 | 3/1978 | Malacheski et al. ............. 222/105 |
| 4,140,117 | 2/1979 | Buckles et al. . |
| 4,157,771 | 6/1979 | Smith . |
| 4,265,241 | 5/1981 | Portner et al. . |
| 4,274,407 | 6/1981 | Scarlett . |
| 4,313,439 | 2/1982 | Babb et al. . |
| 4,337,769 | 7/1982 | Olson . |
| 4,650,469 | 3/1987 | Berg et al. . |
| 4,741,736 | 5/1988 | Brown . |
| 4,756,450 | 7/1988 | Negaty-Hindi et al. ........... 222/105 |
| 4,769,008 | 9/1988 | Hessel . |
| 4,772,263 | 9/1988 | Dorman et al. ................ 604/134 |
| 4,781,689 | 11/1988 | Sealfon et al. . |
| 4,915,693 | 4/1990 | Hessel . |
| 4,950,245 | 8/1990 | Brown et al. . |
| 4,966,585 | 10/1990 | Gangemi . |
| 4,968,301 | 11/1990 | d. Palma et al. ............ 128/DIG. 12 |
| 4,991,742 | 2/1991 | Chang . |
| 5,053,031 | 10/1991 | Bursanyi ..................... 604/891.1 |
| 5,176,641 | 1/1993 | Idriss ........................ 604/131 |
| 5,178,609 | 1/1993 | Ishikawa ..................... 604/135 |

FOREIGN PATENT DOCUMENTS

| | | |
|---|---|---|
| 0 426 319 A2 | 11/1990 | European Pat. Off. . |
| 3507818 | 7/1986 | Germany ................... 604/134 |
| 2197691 | 5/1988 | United Kingdom . |

Primary Examiner—John Weiss
Assistant Examiner—K. M. Reichle
Attorney, Agent, or Firm—Knobbe, Martens, Olson & Bear L.L.P.

[57] ABSTRACT

An infusion pump formed by a fluid containing shell and a pressurizing shell. A conical helical spring is attached within the pressurizing shell. A circular fluid bag with an outlet tube is placed within the fluid containing shell. The bottom of the fluid containing shell is contoured to match the contour of the fluid bag. The fluid containing shell and the pressurizing shell are threadably received within one another so that by screwing the shells together the spring is compressed to pressurize the fluid bag. A platen distributes the force of the spring over a substantially flat area of the bag.

4 Claims, 5 Drawing Sheets

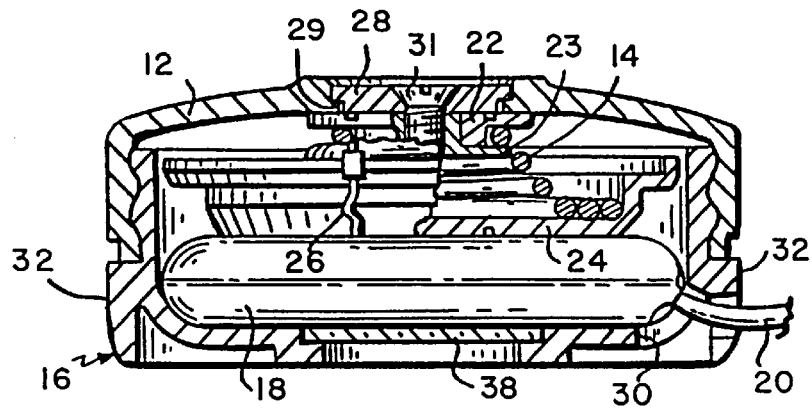
FIG. 4
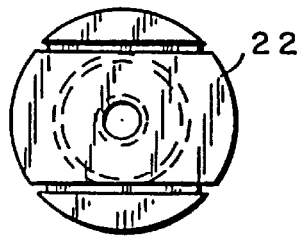
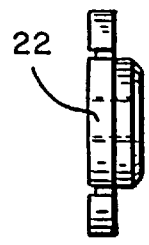
FIG. 5A  FIG. 5B
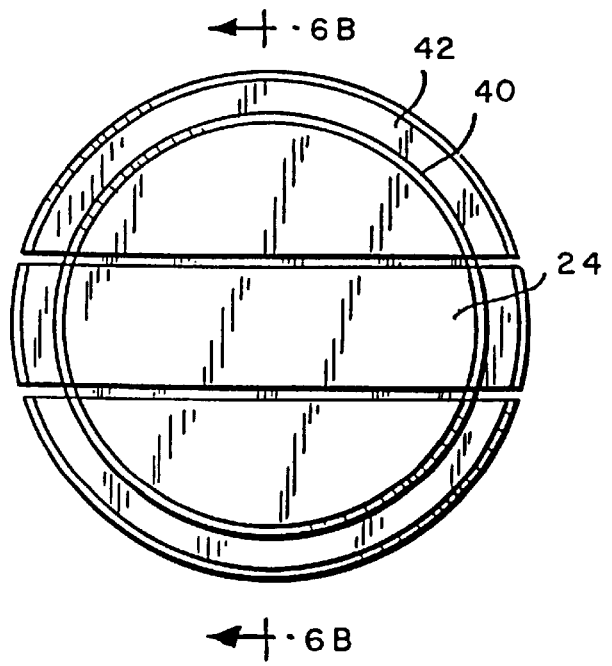
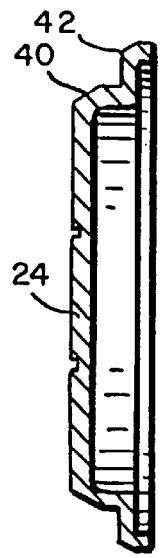
FIG. 6A  FIG. 6B

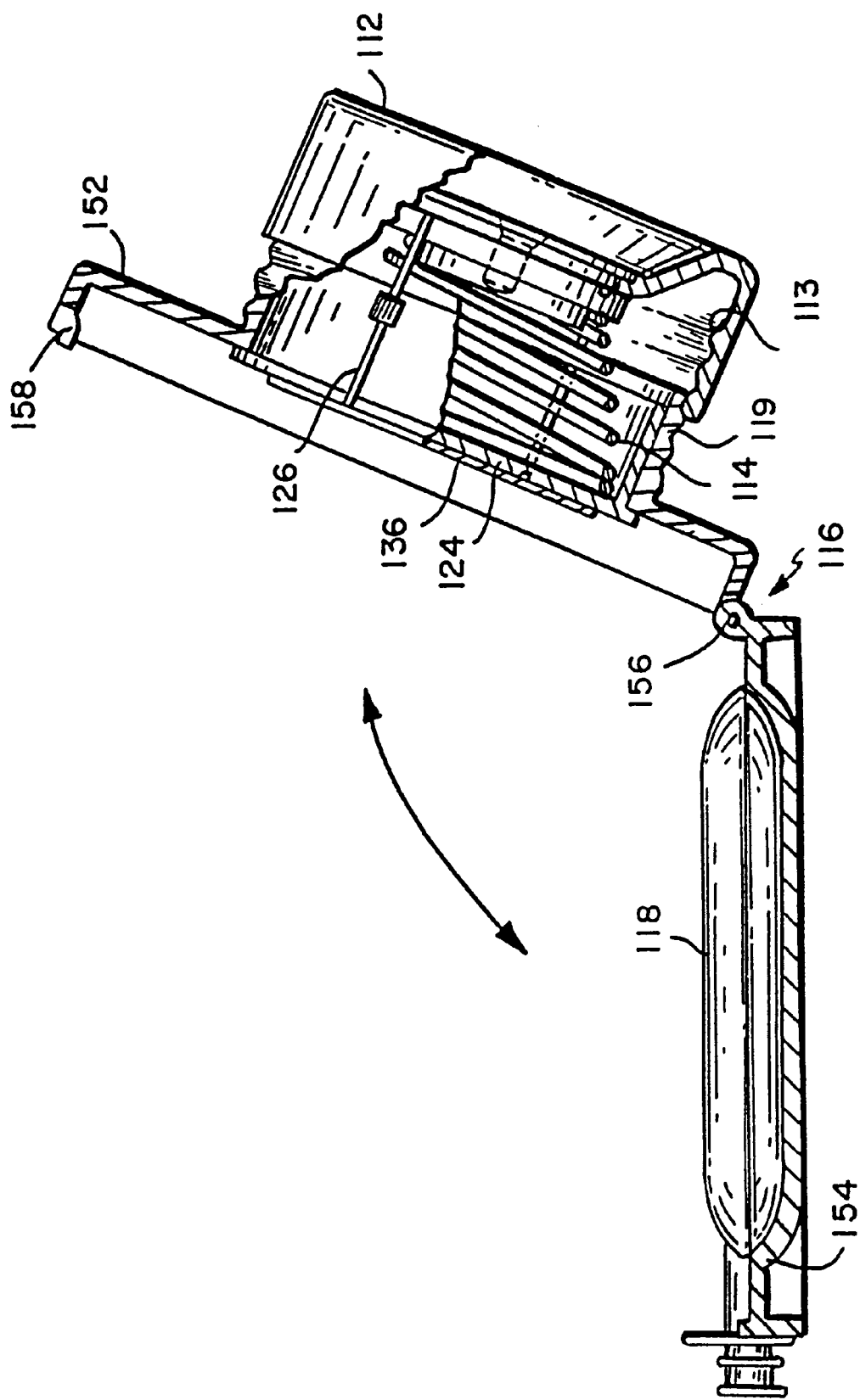

PLATEN PUMP

FIELD OF INVENTION

This invention relates to a low cost drug delivery system useful in delivering drugs, from pliable plastic containers.

BACKGROUND OF THE INVENTION

Many drugs in the health care field are administered to a patient on a continuous basis. Continuous delivery of a drug to a patient was initially achieved by placing a drug delivery bag filled with a drug above the patient and letting gravity force the drug from the bag into the patient. Although this method has proven successful for many applications, its drawbacks included a) an unsteady flow to the patient due to the changing height of the intravenous infusion site relative to the drug bag, b) the awkwardness of requiring the patient to remain below the fluid delivery bag at all times, and c) the constant adjustment of a roller clamp which regulates the flow to the patient. Electromechanical infusion pumps were developed to mitigate these concerns. However, the utility of such pumps was hindered by their bulky size and by their need for a constant source of electricity. These hindrances are especially troublesome in situations where a patient is at home and ambulatory, thus requiring the freedom to move about.

During the past five years, a new style of apparatus has entered the marketplace for controlled delivery of a drug which does not require the use of an electromechanical infusion pump, and thus is suited for the controlled delivery of drugs to patients who are ambulatory. This new style utilizes an inflatable latex rubber balloon housed inside a rigid, clear plastic housing. When the devices are filled with a drug, the latex balloon expands. An administration set is attached to the device and thus acts as the conduit for the drug to the patient. When the balloon is inflated by the drug, the balloon itself becomes the driving force to transfer the drug out of the reservoir to the patient via the drug administration set. Controlled release of the drug at a desired flow rate is achieved by placing an orifice of predetermined diameter in the drug line. These devices generally operate at relatively high pressures of approximately 10 to 15 psi. Examples of the latex balloon system are disclosed in U.S. Pat. Nos. 4,769,008 and 4,915,693 and European Patent Application 0,426,319 A2.

Although the the latex balloon method of drug delivery has certain advantages over the electromechanical infusion pump, the method also has its disadvantages. For example, because the balloon expands in all directions, the shape of the housing enclosing the balloon is round. This round shape does not conform well to the patient when worn in the patient's pocket. Furthermore, some of the latex balloon style devices require a special machine to fill and pressurize the balloon with a drug. Consequently, the pharmacist must use the special machine to load the device. Thus, there exists the need for a safe, economical drug delivery system which could (a) be inconspicuously and comfortably worn by the patient, (b) allow the pharmacist to fill the drug container without the use of a special pressurizing device, (c) allow the nurse or patient to load the drug container into the pressurizing device, (d) allow for reuse of parts of the system.

SUMMARY OF THE INVENTION

The present invention provides a spring housed within a first shell and a collapsible fluid delivery bag housed within a second shell, wherein the reception of the second shell within the first shell compresses the spring against the fluid delivery bag and the subsequent expansion of the spring slowly forces fluid from the fluid delivery bag. The first and second shells are threadably engaged to provide a mechanical advantage to ease compression of the spring when connecting the shells. The drug delivery system of the present invention is preferably constructed as a platen pump. It includes a platen positioned between the spring and the fluid delivery bag to distribute the load from the spring over a substantially flat portion of the bag. The platen is rotatably attached to the first shell so that when the shells are being screwed together the platen does not apply torque to the fluid delivery bag. The fluid delivery bag used with the platen pump of the present invention is advantageously formed as a circular pouch.

This device allows for the use of conventional, low cost manufacturing methods and facilitates reuse of the cylindrical housing for multiple dose drugs such as antibiotics. Other objects and advantages of the invention will become apparent during the following description of the presently preferred embodiment of the invention taken in conjunction with the drawings.

BRIEF DESCRIPTION OF THE DRAWINGS

FIG. 4 is a cross-sectional view of the infusion device of FIG. 1 with the shells fully engaged.

FIGS. 5a and 5b are a plan view and side view, respectively, of the rotatable spring retainer used in the infusion device of FIG. 1.

FIGS. 6a and 6b are a plan view and side view, respectively, of the platen used in the infusion device of FIG. 1.

FIG. 9 is a cross-sectional view of the infusion device of FIG. 8 in an open position.

DETAILED DESCRIPTION OF THE PREFERRED EMBODIMENT

Figure 1:
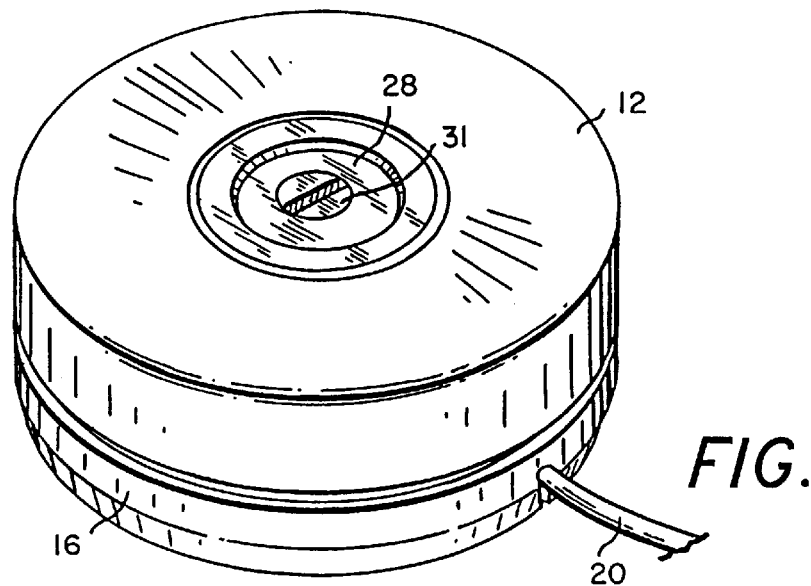
FIG. 1 is an isometric view of the infusion device of the present invention.
Figure 2:
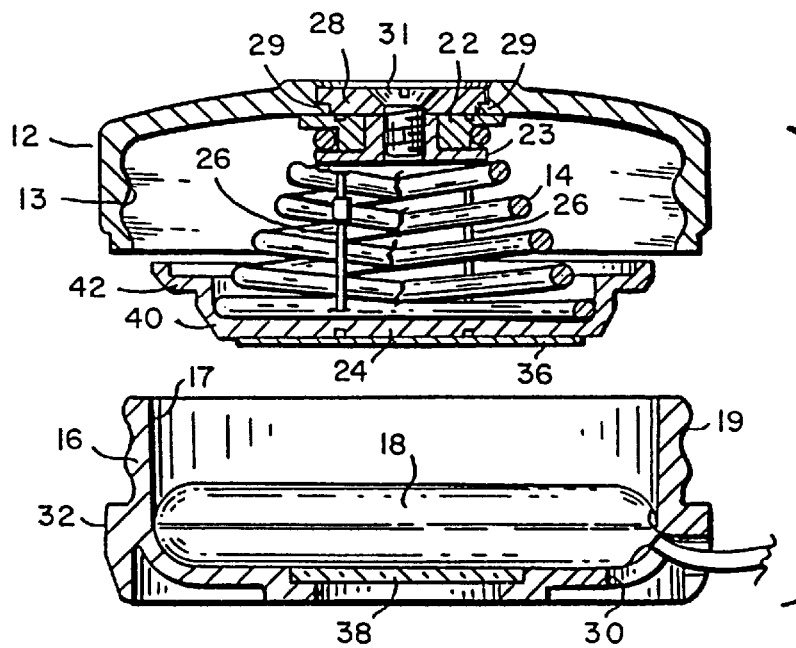
FIG. 2 is a partial cross-sectional view of the infusion device of FIG. 1 with the shells not engaged.
Figure 3:
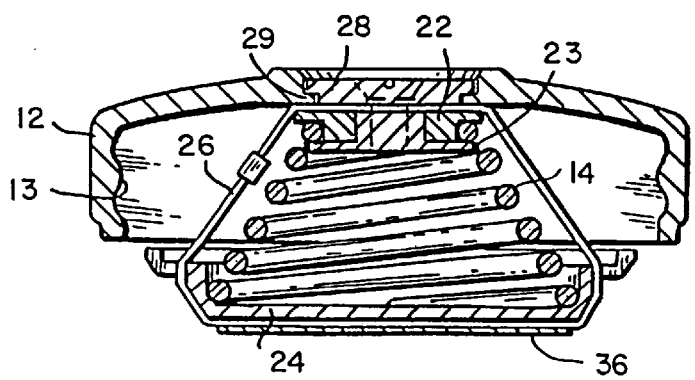
FIG. 3 is a side cross-sectional view of the top shell of FIG. 2.

Referring now to the figures, the infusion device of the present invention shall be called a platen pump. The platen pump is formed in two parts, a pressurizing portion and a fluid containing portion. Each portion is housed in a container or shell. A pressurizing shell 12 includes a helical spring 14. A fluid containing shell 16 includes a chamber 17 for housing a fluid delivery bag 18. When the pressurizing shell 12 and the fluid containing shell 16 are connected to form the enclosed pump, the fluid delivery bag is pressurized by the spring 14. Fluid is thus continuously forced out of the bag 18 through an outlet tube 20 in fluid communication therewith. Controlled fluid flow is achieved with a small diameter fixed orifice 46 located at the end of the tube. The pump of FIG. 1 is 3½" in diameter and 1.7" high. A selectively releasable clamp 34 may be applied to the outlet tube to stop fluid flow from the pump. Releasing the clamp restores fluid flow.

In accordance with the presently preferred embodiment of the invention, the pressurizing means is a conical helical coil spring 14. The spring is formed from stainless steel or a suitable spring material. The coils of the spring are made progressively larger so that when compressed the spring coils can overlap to compress to a lower height than a conventional compression spring. When the spring is expanded it takes on a conical shape. The conical helical spring exerts the greatest force when it is fully compressed. The force is approximated by the equation F=kx, where k is the spring rate and x is the distance the spring is compressed. Because it is desirable to have the force exerted on the drug container be nearly the same when the container is full as when it is nearly empty, it is preferred that the free length of the spring be several times the height of the pump. Thus, the working length is but a fraction of its total free length. This insures that the force applied by the spring is kept within an acceptable tolerance from the beginning to the end of the infusion. In accordance with the presently preferred embodiment, the change in force exerted by the spring over the course of an infusion as compared to the initial force it exerts when compressed against a full fluid delivery bag is less than 20%. In accordance with the invention, the spring length should be selected such that the change in force over the course of an infusion is less than 30%. In addition to a conventional compression spring, this concept would apply to a leaf spring, if it was used instead, where the deflection in the leaf spring is but a fraction of the total possible deflection.

A flexible cable retainer 26 encircles the spring 14 to set its initial compressed height and also to prevent it from expanding beyond the height of the pressurizing shell 12. In the presently preferred embodiment, two cables 26 are used. Thus, the spring 14 does not bear against the fluid delivery bag when the pressurizing shell 12 is initially engaged with the fluid containing shell 16. This makes it easy for a user to bring the two shells together. With the spring in its initially compressed state, the force differential between the full position shown in FIG. 4 and empty position with the bag squeezed to a completely collapsed position is less than 30% of the initial force in the full position. While the conical helical coil spring is preferred, it would be possible to make a platen pump with a leaf spring, a pressurized bladder, a standard helical compression spring or a canister of pressurized gas to act as the pressurizing means.

The smallest coil of the spring is rotatably attached to the closed end of the pressurizing shell 12. The spring is attached to the pressurizing shell by a rotatable connector including a spring retainer 22, an anchor pivot 28, a spring stop 23 and a screw 31. The anchor pivot 28 is seated on a shoulder 29 encircling a hole in the top of the pressurizing shell 12. The anchor pivot 28 is free to rotate on the shoulder 29. The rotatable spring retainer 22 is mounted to an anchor pivot 28. The spring retainer 22 centers the spring to the shell. A spring stop 23 clamps the end coil of the spring to the spring retainer and prevents the spring from dislodging from the spring retainer 22. The screw 31 holds the anchor pivot 28 and the spring stop 23 together. The spring retainer 22 is sandwiched between the anchor pivot and the spring stop.

Preferably, in the present invention, a fluid delivery bag is pressurized to only about 5 psi which requires only about 30 pounds of force. In order that health personnel or the patient can pressurize the pump without assistance, the pressurizing shell 12 and fluid containing shell 16 are threadably engaged. In the presently preferred embodiment, the pressurizing shell has inner helical threads 13 and the fluid containing shell has outer helical threads 19. By increasing the number of threads per inch, the axial force provided by the threads can be increased for a given torque. The presently preferred embodiment uses four (4) threads per inch so that it is relatively easy to screw the shells together to fully pressurize the pump. The threads provide a mechanical advantage so that a modest amount of torque can generate sufficient amounts of axial load to compress the spring.

A platen 24 is located between the spring 14 and the fluid delivery bag 18 when the two shells are connected. The platen 24 distributes the pressure from the spring 14 over the bag. The presently preferred platen is made of polycarbonate. The platen has a bottom flat portion which extends over an area no greater than a substantially flat central portion of the fluid delivery bag. This serves to keep the contacting surface areas fairly constant over the course of the entire infusion to help minimize changes in pressure on the fluid bag. The platen 24 is held against the helical coil within the pressurizing shell 12 by the flexible restraining cable 26. The cable 26 is preferably made from multi-strand stainless steel. It is looped about the rotatable retainer 22 and the platen 24. Preferably, two cable loops 26 are used. Grooves are provided in the retainer 22 and platen 24 to accommodate the cables 26. A plastic label 36 may be adhered to the bottom of the platen 24 thereby holding the cables 26 within their grooves.

The spring 14, platen 24 and rotatable connector are secured to one another by the cables 26. The anchor pivot 28, the spring 14, spring retainer 22, spring stop 23, the platen 24 and the cable 26 all rotate freely about the axis of the pressurizing shell. Thus, when the pressurizing shell is rotated with respect to the fluid delivery shell to thread the two together, the pressurizing shell turns independently of the platen 24. The platen 24 should remain stationary with respect to the fluid delivery bag so that no torsional load is imparted on the bag. In order to mechanically prevent twisting the fluid delivery bag 18 when the two shells are screwed together, anti-rotation tabs can be attached to the outer edge of the platen 24. The tabs would extend out radially to engage slots in the wall of the fluid containing shell 16. The tabs would be guided in the slot, thus preventing the platen from turning with respect to the fluid containing shell. It has been found that rotatably attaching the spring and platen to the pressurizing shell is sufficient to avoid applying undesirable torque to the fluid delivery bag. The tabs and slots are not required.

Figure 11:
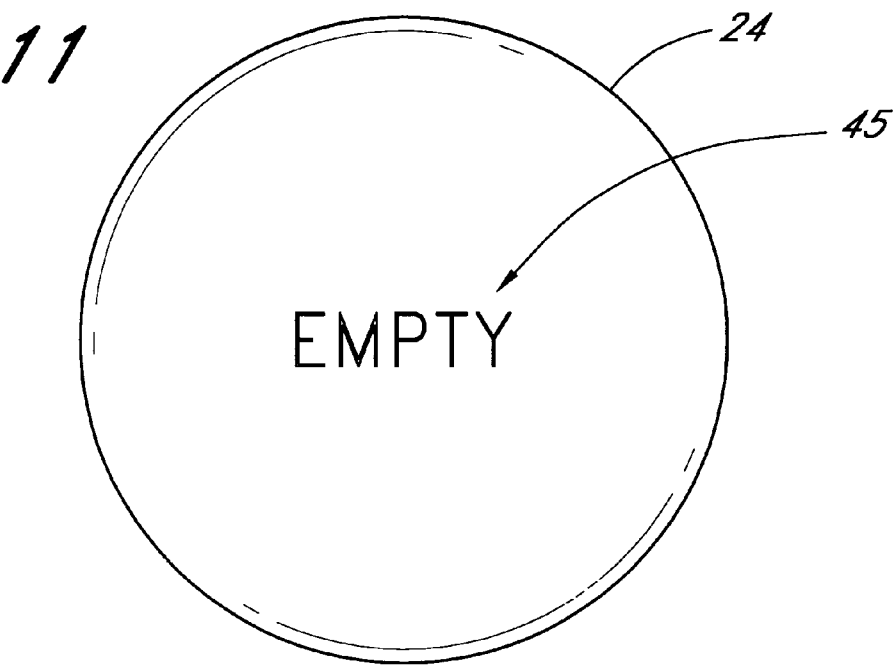
FIG. 11 is a plan view of a platen having a legend reading "EMPTY".
Figure 12:
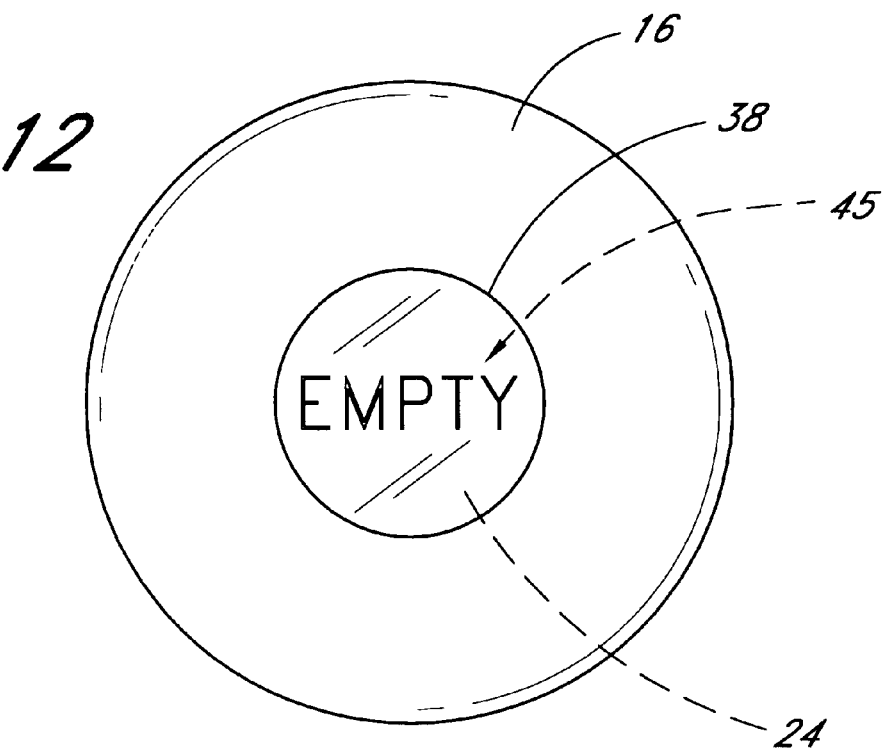
FIG. 12 is a plan view of the platen pump of FIG. 2 illustrating the legend of FIG. 11 as seen through the transparent window when a fluid delivery bag contained within the pump is empty.

Because it is desirable to have a device which allows the patient to examine the volume of fluid still retained in the fluid delivery bag so that the patient can determine when the bag is empty, preferred embodiments of the present invention utilize a clear plastic window 38 in the bottom of the fluid containing shell 16. Due to cost and safety considerations, especially preferred embodiments of the present invention use a clear plastic, such as polycarbonate, as the window material. A legend 45 such as the word "Empty" is printed on the bottom side of the platen 24, as shown in FIG. 11, or on the label 36. Advantageously, the legend will be fuzzy or illegible when viewed through the transparent window when there is liquid in the fluid delivery bag. When the bag has been emptied and the platen lies flat against the layers of the bag and the bottom of the chamber 17, the legend on the platen 24 comes into focus through the bottom of the fluid containing shell due to the translucent nature of the fluid delivery bag, as shown in FIG. 12. This can be used to provide a clear indication of when the fluid bag is empty.

To the extent possible, it is desirable to maintain a relatively constant flow rate throughout an infusion with the platen pump. In order to minimize changes in the internal pressure within the fluid delivery bag, the surface area of contact between the bag and the rigid surfaces pressing against it should be kept constant. In accordance with the present invention, the bottom of the chamber 17 in the fluid containing shell 16 is contoured to evenly support the bottom of the bag over its entire area. Thus, the surface contact against the bottom of the bag remains constant during the full stroke of the platen. In the figures, a curved contour is shown about the periphery of the chamber 17. The bag 18 when filled with fluid matches this curved contour to receive support over its entire area. The contour of the chamber 17 could also be achieved with a 45° angle about the periphery. While the bag 18 might not completely fill the corner formed by the angle, the contour of the surface areas should be adequate to provide substantial support and contact with the bag's entire area.

It is also important that the contact area of the platen 24 against the bag remain constant. Therefore, the platen 24 has a bottom flat surface which does not extend beyond a flat central portion of the fluid delivery bag. If only the flat portion of the platen were to act on the bag, a residual fluid would remain in the bag about its periphery at the end of the infusion. In order to more completely deliver the fluid from the bag, the platen has a chamfered edge 40 and a recessed outer ring 42. These portions of the platen roughly match the contour of the periphery of the bottom of the chamber 17. A platen 24 with a periphery that conforms more exactly to the contour of the chamber bottom could also be used. Near the end of an infusion, as the platen 24 descends towards the chamber bottom, fluid which builds up about the periphery of the bag 18 is pushed out by the edge 40 and the recessed ring 42.

An opening 30 is provided in the fluid-containing shell through which the outlet tube connected to the fluid delivery bag 18 can be extended. An outer wall 32 of the fluid containing shell can be provided to serve as a grip. When screwing the shells together, one hand holds the outer wall of the pressurizing shell and the other hand holds the outer wall 32 of the fluid containing shell 16.

Figure 7:
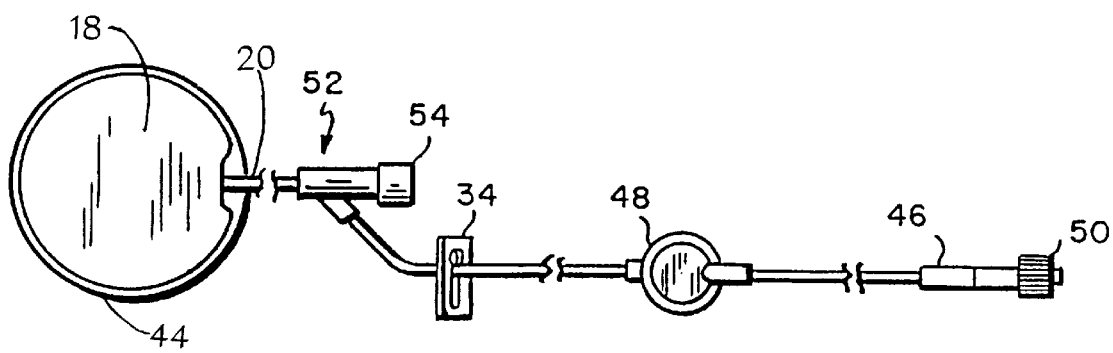
FIG. 7 is a plan view of the fluid delivery bag of the present invention.

The two shells of the pump are circular in shape to permit threadable engagement. Referring now to FIG. 7, the fluid delivery bag 18 for use in the platen pump is a circular pouch connected to an outlet tube. The circular pouch, advantageously, has no corners. Thus, the seam 44 of the bag is uniformly stressed. To assist in achieving uniformity of pressure in the bag, the periphery of the bag has a curved contour when filled. The center portion of the bag is substantially flat so that the contacting surfaces between the platen and the bag can remain relatively constant throughout an infusion. The bag is made from a suitable pliable biocompatible plastic material, such as a class VI, PVC biocompatible plastic. The bag is formed from two circular sheets that are RF welded together around their circumference. The round shape of the bag achieves uniform stress on the welded seam.

The outlet tube 20 is connected to the bag 18. The tube 20 may lead to a restricted orifice 46 which restrains the flow of fluid from the delivery bag when it is pressurized. Orifices of 0.004 to 0.008" diameter are presently contemplated. In order to prevent the orifice from becoming blocked, it is recommended that a particulate filter 48 be inserted in the outlet tube to stop the flow of particles which might occlude the orifice. The orifice provides a relatively constant fluid flow. As an alternative to the restricted orifice, a length of tubing of known diameter, e.g., an 18 in. length of 0.015" tube can be substituted. In order to facilitate filling the fluid delivery bag, a Y-injection site 52 may be inserted into the outlet tube 20. The Y-injection site 52 includes a latex rubber self-sealing septum 54 through which a needle may be inserted to inject fluid into the bag.

The end of the outlet tube can be connected to a luer adapter 50. The adapter is a threadably engaged connector. It is designed to mate with a threadably engaged disconnect on an IV line. In order to permit reusability of an infusion set, the outlet tube 20 of the fluid delivery bag can be directly connected to a second luer adapter 50 (not illustrated) approximately 3 inches from the drug bag. A clamp would be used on the tube between the bag and the luer adapter 50. Fluid may be injected in through the luer adapter 50 so a Y-injection site would not be needed. When the drug has been expended, a new drug bag may be attached to the IV set, thus reusing the IV set for multiple doses over a 24 to 48 hour period.

In practicing the invention, the clamp 34 is used to close the outlet tube on an empty drug delivery bag. A needle pierces the septum 54 to inject fluid into the drug delivery bag. The bag when full should have a substantially flat top and bottom central portion when resting on a flat surface. The needle is removed. The bag, with its permanently affixed IV line, is placed in the chamber 17 of fluid containing shell 16 with the IV line passing through the opening 30 in the bottom of the shell. When the upper and lower shells are brought together, the threads should preferably engage initially before the platen 24 pressurizes the bag. The two shells are then simply screwed together until a stop position is reached. At this point, the drug bag is fully pressurized. The IV output line is purged of air by opening the clamp 34 and allowing fluid to flow. Once the fluid stream ejects slightly, the tube can be reclamped. The output line is then connected to a catheter line or needle for administering an infusion to a patient. Releasing the clamp initiates fluid flow. When the legend on the platen 24 comes into focus through the window 38 in the fluid containing shell 16, the bag has been emptied. The output line is removed or disconnected from the patient. The two shells are then unscrewed and the drug container and IV line are discarded. The pump can be reused.

Figure 8:
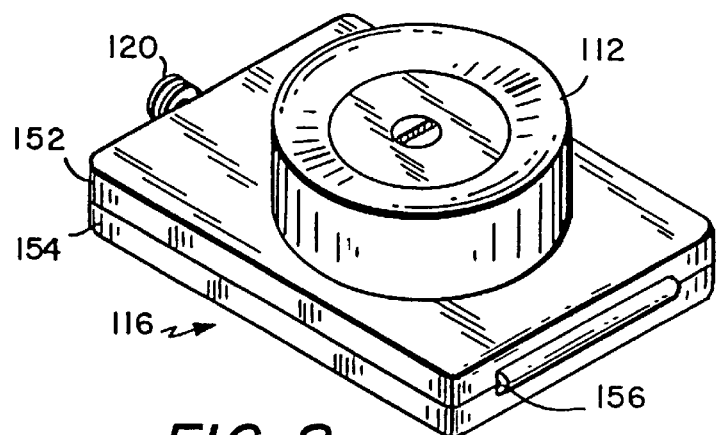
FIG. 8 is an isometric view of an alternate embodiment of the infusion device of the present invention.
Figure 10:
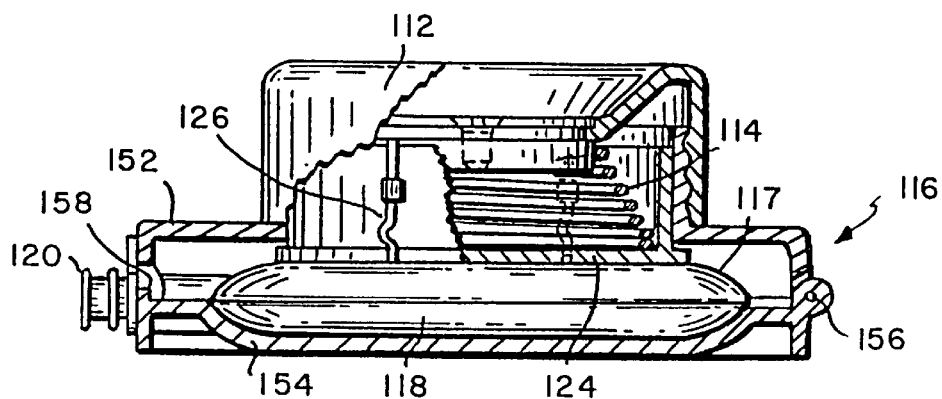
FIG. 10 is a cross-sectional view of the infusion device of FIG. 8 in a closed position.

Referring now to FIGS. 8–10, an alternate embodiment of the present invention is illustrated. The numerical labels in the drawings are 100 higher than corresponding elements in the first embodiment. When it is desired to use a conventional rectangular drug delivery bag 118, the alternate embodiment can be used. The fluid containing shell 116 of the alternate embodiment is provided with a rectangular chamber to accommodate the rectangular drug delivery bag. The fluid containing shell 116 is formed by an upper portion 152 and lower portion 154 attached at one end by a hinge 156. The opposite ends are connected by a latch 158 when the upper and lower portions are closed. The upper portion 152 includes a threaded cylindrical wall 119 for interfacing with the threaded wall 113 of the pressurizing shell 112. The platen 124 attached to the spring 114 of the pressurizing shell 112 is made rectangular to fit over the substantially flat center portion of the rectangular bag.

To operate the platen pump of the alternate embodiment, the pressurizing shell is unscrewed and loosened on the fluid containing shell. The fluid containing shell is opened about its hinge. A fluid delivery bag is inserted. The fluid containing shell is closed at its latch. The pressurizing shell can then be screwed onto the fluid containing shell to pressurize the drug delivery bag.

Of course, it should be understood that various changes and modifications to the preferred embodiments described above will be apparent to those skilled in the art. If the mechanical advantages of the threads can be done without, the pressurizing shell and fluid containing shell could be held together by latches. As already mentioned, other methods of pressurization may be used in place of the conical helical spring. These and other changes can be made without departing from the spirit and scope of the invention and without diminishing its attendant advantages. It is therefore intended that such changes and modifications be covered by the following claims.

We claim:

1. An infusion apparatus comprising:

a fluid delivery bag connected to an outlet tube, said fluid delivery bag having a bottom side and a top side, said bottom side having a curved contour about its periphery and said top side having a substantially flat central portion;

a first shell having threads and a closed end;

a second shell threadably engaged with said first shell, said second shell having a chamber for receiving said delivery bag, said chamber having a bottom contour which approximates the contour of said bottom side of said fluid delivery bag;

a conical helical spring, having a first coil end attached to said closed end of said first shell, and a second coil end; and a platen having a non-planar bottom surface configuration which is complementary to said bottom contour of said second shell and a top surface, said top surface of said platen attached to said second end of said helical spring, wherein said helical spring exerts a force on said top surface of said platen and wherein said bottom surface of said platen exerts a force on said top side of said fluid delivery bag when said fluid delivery bag is placed in said chamber of said second shell.

2. The apparatus of claim 1, wherein said second coil end is larger than said first coil end.

3. An infusion apparatus comprising:

a fluid delivery bag connected to an outlet tube, said fluid delivery bag having a bottom side and a top side, said bottom side having a curved contour about its periphery and said top side having a substantially flat central portion;

a first shell having threads and a closed end;

a second shell threadably engaged with said first shell, said second shell having a chamber having a bottom contour which approximates the contour of said bottom side of said fluid delivery bag;

a conical helical spring, having a first coil end attached to said closed end of said first shell, and a second small coil end; and a platen having a non-planar bottom surface configuration which is complementary to said bottom contour of said second shell and a top surface, said top surface of said platen attached to said second end of said helical spring, wherein said helical spring exerts a force on said top surface of said platen and wherein said bottom surface of said platen exerts a force on said flat central portion of said fluid delivery bag when said fluid delivery bag is placed in said chamber of said second shell.

4. An infusion apparatus comprising:

a fluid delivery bag connected to an outlet tube, said fluid delivery bag having a top surface with a substantially flat central portion;

a first shell having a closed end;

a helical spring attached to said closed end of said first shell;

a second shell threadably engaged with said first shell and having a chamber therein for holding said fluid delivery bag between said first shell and said second shell; and a platen attached to said helical spring, said platen having a non-planar bottom surface configuration which is complementary to a bottom contour of said chamber and a top surface, said platen for distributing a force exerted from said spring to the substantially flat central portion of said fluid delivery bag, wherein when said second shell is engaged with said first shell, said helical spring exerts force on said top surface of said platen and said bottom surface of said platen exerts force on said fluid delivery bag so as to force a fluid contained with said fluid delivery bag through the outlet tube.

* * * * *